United States Patent [19]

Schmalstieg et al.

[11] Patent Number: 5,142,081
[45] Date of Patent: Aug. 25, 1992

[54] PROCESS FOR THE PREPARATION OF O-SILYLATED HYDROXYL COMPOUNDS AND THEIR USE FOR THE PREPARATION OF ISOCYANATES CONTAINING ESTER GROUPS

[75] Inventors: Lutz Schmalstieg; Josef Pedain, both of cologne; Klaus Nachtkamp, Düsseldorf, all of Fed. Rep. of Germany

[73] Assignee: Bayer Aktiengesellschaft, Leverkusen, Fed. Rep. of Germany

[21] Appl. No.: 596,173

[22] Filed: Oct. 10, 1990

[30] Foreign Application Priority Data

Oct. 12, 1989 [DE] Fed. Rep. of Germany ....... 3934100

[51] Int. Cl.$^5$ .......................... C07F 7/04; C07F 7/08
[52] U.S. Cl. ................... 556/471; 549/214; 556/443; 556/410; 560/301
[58] Field of Search ............... 556/471, 443; 549/214; 560/301

[56] References Cited

U.S. PATENT DOCUMENTS 4,207,247 6/1980 Knollmueller ...................... 556/463
4,379,766 3/1983 Mack ................................. 260/413

FOREIGN PATENT DOCUMENTS 3505746 12/1985 Fed. Rep. of Germany .
3634248 4/1988 Fed. Rep. of Germany .

OTHER PUBLICATIONS

Kashutina et al. Russ. Chem. Rev. 44,733, 1955.
Ialonde et al. Synthesis 1985, 817.
Langer et al. J. Org. Chem. 23,50 (1958).
Chemical Abstracts, vol. 96, 1982, p. 620, No. 6787r.
Chemical Abstracts, vol. 99, 1983, p. 649, No. 22784e.
M. V. Kashutina, S. L. Ioffe, and V. A. Tartakovskii, Russian Chemical Reviews, 44, 1975, pp. 733–747.
M. Lalonde, T. H. Chan., Synthesis 1985, pp. 817–845.
Houben–Weyl, Methoden der Organischen Chemie, vol. VI, pp. 739–741.
Houben–Weyl Methoden Der Organischen Chemie, vol. 13/5–p. 190.
Langer, Connell and Wender, Journal of Organic Chemistry, vol. 23, 1958, pp. 50–58.

Primary Examiner—Jose G. Dees
Assistant Examiner—Joseph M. Conrad
Attorney, Agent, or Firm—Joseph C. Gil; Thomas W. Roy

[57] ABSTRACT

This present invention relates to a process for the preparation of O-silylated aliphatic hydroxyl, compounds by the reaction of aliphatic hydroxyl compounds with triorganochlorosilanes and removal of the resulting gaseous hydrogen chloride from the reaction mixture, characterized in that the reaction is carried out in the presence of phase transfer catalysts in the absence of solvent.

The invention also relates to the use of the O-silylated hydroxyl compounds obtained by this process as starting materials for the preparation of isocyanates containing ester groups by a reaction with isocyanato carboxylic acid chlorides.

11 Claims, No Drawings

PROCESS FOR THE PREPARATION OF O-SILYLATED HYDROXYL COMPOUNDS AND THEIR USE FOR THE PREPARATION OF ISOCYANATES CONTAINING ESTER GROUPS

BACKGROUND OF THE INVENTION

1. Field of the Invention

This invention relates to a new process for the preparation of O-silylated aliphatic hydroxyl compounds by the reaction of aliphatic hydroxyl compounds with triorgano-chlorosilanes in the presence of phase transfer catalysts and to the use of the resulting O-silyated compounds as starting materials for the preparation of isocyanates containing ester groups.

2. Description of the Prior Art

Numerous processes for the silylation of hydroxyl compounds are known (see e.g. M. V. Kashutina, L. S. Ioffe, K. A. Tartakovskii, Russ. Chem. Rev. 44, 733 (1955) or M. Ialonde, C. H. Chan, Synthesis 1985, 817 or Houben-Weyl, Methoden der organischen Chemie, Volume VI/Ib, page 739 and Volume 13/5, page 190).

The most commonly used silylating agents are triorganochlorosilanes. The known processes for the preparation of aliphatic O-silylated compounds by the reaction of aliphatic hydroxyl compounds with triorganochlorosilanes in the liquid phase have the disadvantage that satisfactory yields can only be obtained if the hydrogen chloride formed is bound by bases since the reaction of the starting materials must otherwise be expected to be incomplete or side products are liable to be formed. Separation of the salts produced leads to losses in yields and constitutes an additional and therefore cost increasing procedure. Further, the formation of salts in equimolar quantities is a disadvantage from an ecological point of view.

Silylated amides are also frequently used for the silylation of hydroxyl groups In this case, again, the desilylated amide formed in the process of silylation must be removed from the reaction mixture by an expensive procedure.

Silylation with hexamethyl disilazane also has disadvantages. The preparation of hexamethyl disilazane from trimethylchlorosilane and ammonia is accompanied by the formation of ammonium chloride and secondly, our own experiments have shown that some hydroxyl compounds are impossible to silylate with hexamethyl disilazane.

Silylation by the combined use of trimethylchlorosilane and hexamethyl disilazane is also accompanied by the formation of ammonium chloride in an equimolar quantity.

The process described in DE-OS 35 05 746 for silylation by means of trimethylsilyl cyanide is also disadvantageous because of the release of toxic hydrocyanic acid.

Although O-silylated hydroxyl compounds, in particular O-silylated aliphatic polyhydroxyl compounds, are interesting intermediate products for the preparation of polyisocyanates containing ester groups (see e.g. DE-OS 3 634 248), the problems mentioned above have previously prevented their use on a large commercial scale.

It was therefore an object of the present invention to provide a new process for the preparation of O-silylated aliphatic hydroxyl compounds which would be free from these difficulties and would in particular enable the above mentioned compounds to be prepared in high yields without the corresponding production of large quantities of salts or of toxic decomposition products.

This object has been achieved by the process according to the present invention described below.

The process according to the present invention is based on the surprising finding that when so called phase transfer catalysts are used, aliphatic hydroxyl compounds react with triorganochlorosilanes with the release of gaseous hydrochloric acid until one of the starting components has been used up. This must be regarded as distinctly surprising since in the case of aliphatic hydroxyl compounds it is known that establishment of an equilibrium according to the following equation

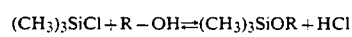

is favored by the solubility of hydrogen chloride in the alcohol component which prevents complete silylation. Further, it is known that hydrogen chloride has a tendency to react with the hydroxyl compounds to form undesirable by-products (alkyl chlorides), which again leads to a loss of yield (S. H. Langer, C. Connell, I. Wender, J. Org. Chem. 23, 50 (1958)). In the reaction between phenols and triorganochlorosilanes, these side reactions occur to a much smaller extent but the reaction is still accelerated by the catalysts used according to the present invention.

SUMMARY OF THE INVENTION

This present invention relates to a process for the preparation of O-silylated aliphatic hydroxyl compounds by the reaction of aliphatic hydroxyl compounds with triorganochlorosilanes and removal of the resulting gaseous hydrogen chloride from the reaction mixture, characterized in that the reaction is carried out in the presence of phase transfer catalysts.

The invention also relates to the use of the O-silylated hydroxyl compounds obtained by this process as starting materials for the preparation of isocyanates containing ester groups by a reaction with isocyanato carboxylic acid chlorides.

DETAILED DESCRIPTION OF THE INVENTION

Any aliphatic hydroxyl compounds may be used as starting materials for the process according to the invention, i.e. any organic compounds containing aliphatically bound hydroxyl groups.

Suitable aliphatic hydroxyl compounds are low molecular weight, monohydric to octahydric alcohols having a molecular weight of 32 to 342 and relatively high molecular weight polyhydroxyl compounds which have a molecular weight above 342 and are known from polyurethane chemistry, i.e., hydroxyl-containing polyaddition, polycondensation or polymerization products. The aliphatic hydroxyl compounds used may contain functional groups which are free from active hydrogen atoms and are inert towards triorganochlorosilanes and hydrogen chloride. The hydroxyl groups may be attached to primary, secondary or tertiary carbon atoms. The term "aliphatic" is defined throughout the application to include araliphatic alcohols such as benzyl alcohol; cycloaliphatic alcohols such as cyclohexanol; and cyclic sugars and sugar alcohols.

Examples of monohydric to octahydric alcohols having a molecular weight of 32 to 342 and suitable as starting materials for the process according to the invention include methanol, ethanol, n-propanol, 2-propanol, n-butanol, 2-butanol, t-butanol, n-pentanol, 3-methyl-1-butanol, neopentyl alcohol, n-hexanol, 2-ethyl-1-butanol, n-octanol, 2-ethyl-1-hexanol, ethylene glycol, propylene glycol, butane-1,4-diol, hexane-1,6-diol, 2,2,4-trimethyl-pentane diol, glycerol, trimethylol ethane, trimethylol propane, pentaerythritol, mannitol, sorbitol, formitol, monosaccharides such as fructose or glucose, disaccharides such as maltose or saccharose, low molecular weight alcohols containing ether groups (such as diethylene glycol, triethylene glycol, dipropylene glycol or tripropylene glycol and other low molecular weight alkoxylation products of the polyhydric alcohols exemplified above, provided that their molecular weight does not exceed 342), low molecular weight polyols containing ester groups (such as the hydroxyl group-containing low molecular weight esterification products of the polyhydric alcohols mentioned above with polybasic carboxylic acids such as adipic acid, phthalic acid, tetrahydrophthalic acid and/or hexahydrophthalic acid), low molecular weight polyols containing urethane groups (such as the low molecular weight products of reaction of the polyhydric alcohols mentioned above with subequivalent quantities of organic polyisocyanates such as hexamethylene diisocyanate or 2,4- and/or 2,6-diisocyanato toluene) and mixtures of these low molecular weight alcohols. The polyhydric alcohols mentioned above and having a functionality of 2 to 8 are preferable to the monohydric alcohols mentioned above.

The relatively high molecular weight hydroxyl compounds, i.e., compounds with a molecular weight above 342, include polyaddition, polycondendsation and polymerization products containing at least two alcoholic hydroxyl groups which are known in polyurethane chemistry.

Suitable relatively high molecular weight polyhydroxyl compounds include those which have a molecular weight ($M_n$, which may be obtained from an end group analysis) of 343 to 10,000, preferably from 1000 to 5000, and contain 2 to 8, preferably 2 or 3 hydroxyl groups per molecule.

Examples of suitable relatively high molecular weight polyhydroxyl compounds include the polyether polyols which are known from polyurethane chemistry and may be obtained by the alkoxylation of suitable starter molecules such as water, the simple polyhydric alcohols previously disclosed and mixtures thereof. Suitable alkylene oxides include in particular ethylene oxide, propylene oxide and 1,2-butylene oxide which may also be used as mixtures or in any sequence in the alkoxylation reaction.

Also suitable as the relatively high molecular weight polyhydroxyl compounds are the polyester polyols which are known from polyurethane chemistry and may be obtained by the reaction of the polyhydric polyols previously disclosed with subequivalent quantities of polybasic acids such as adipic acid, phthalic acid, isophthalic acid, tetrahydrophthalic acid, hexahydrophthalic acid, the anhydrides of such acids and mixtures of such acids or acid anhydrides.

Polyesters of lactones such as ε-caprolactone or hydroxy carboxylic acids such as ω-hydroxy caproic acid may also be used as relatively high molecular weight polyhydroxyl compounds as well as hydroxyl group-containing polycarbonates such as those obtained by the reaction of the diols mentioned above with phosgene or diaryl carbonates such as diphenyl carbonate (DE-AS 1 694 080, 1 915 908, 2 221 751 or DE-OS 2 605 024).

Polyester-polycarbonates containing hydroxyl groups such as those obtained according to DE-AS 1 770 245 are also suitable. These compounds may be prepared by the reaction of ε-caprolactone with polyols such as hexane-1,6-diol followed by reaction of the resulting ester glycols with diphenyl carbonate.

Also suitable for use as relatively high molecular weight aliphatic hydroxyl compounds are the polyhydroxy polyacrylates known from polyurethane chemistry. These compounds have a molecular weight ($M_w$, determined by gel permeation chromatography using polystyrene as the standard) of 800 to 50,000, preferably 1000 to 20,000 and a hydroxyl group content of 0.1 to 12% by weight, preferably 1 to 10% by weight. They are prepared by the copolymerization of olefinically unsaturated monomers such as styrene, (meth)acrylonitrile or $C_1$ to $C_8$ alkyl esters (such as methyl, ethyl, n-propyl, n-butyl, n-hexyl, 2-ethylhexyl or isooctyl esters) of (meth)acrylic acid with monomers containing hydroxyl groups (such as 2-hydroxyethyl, 2-hydroxypropyl, 3-hydroxypropyl, 4-hydroxypropyl, or 6-hydroxyhexyl esters of (meth)acrylic acid). Natural polyols such as castor oil may also be used.

Compounds corresponding to the following formula are suitable triorganochlorosilanes for the process according to the invention:

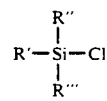

wherein
R', R'' and R''', may be the same or different and represent alkyl, aryl, alkaryl and/or aralkyl groups.

These groups are preferably $C_1$ to $C_6$ alkyl groups, phenyl groups, tolyl groups or benzyl groups, more preferably $C_1$ to $C_4$ alkyl groups and most preferably methyl groups. Examples of triorganochlorosilanes which are suitable for use in accordance with the present invention include trimethylchlorosilane, t-butyl-dimethylchlorosilane, i-propyl-dimethylchlorosilane, triethylchlorosilane, chlorotribenzylsilane, chlorotributylsilane, chlorotriisopropylsilane, chlorotrihexylsilane, chlorotriisobutylsilane and chlorotriphenylsilane.

Suitable phase transfer catalysts include the known quaternary ammonium and phosphonium salts and crown ethers. Quaternary ammonium and phosphonium salts are preferably used.

Suitable compounds include those corresponding to the formula.

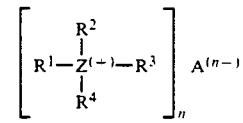

wherein
Z represents nitrogen pr phosphorus,
$R^1$, $R^2$, $R^3$ and $R^4$ may be the same or different and represent aliphatic, cycloaliphatic, aromatic or araliphatic hydrocarbon groups, provided that the sum of the carbon atoms in these groups is 8 to 28, n represents 1 or 2 and A represents an anion of an acid with a valency of n or a hydroxide anion.

Particularly suitable are ammonium salts corresponding to the above formula wherein Z represents nitrogen, $R^1$, $R^2$, $R^3$ and $R^4$ may be the same or different and represent aliphatic hydrocarbon groups containing 1 to 18 carbon atoms, phenyl groups or benzyl groups, provided that the sum of the carbon atoms in these groups is 8 to 24 and at least three of the groups are aliphatic hydrocarbon groups, n represents 1 and A represents a bromide, chloride or iodide anion.

Examples of suitable phosphonium salts include tributylhexadecyl phosphonium bromide, ethyltriphenyl phosphonium bromide, tetraphenyl phosphonium chloride, benzyltriphenyl phosphonium chloride and tetrabutyl phosphonium chloride.

Examples of quaternary ammonium salts include benzyltriethyl ammonium bromide; tetrabutyl ammonium chloride, bromide, iodide or hydroxide; benzyltrimethyl ammonium chloride or hydroxide; cetyltrimethyl ammonium bromide or chloride; benzyltributyl ammonium bromide; tetra-n-pentyl ammonium chloride; tetra-n-hexyl ammonium chloride; trioctylpropyl ammonium chloride; tetra-n-butyl ammonium hydrogen sulphate; and tetra-n-hexyl ammonium hydrogen sulphate. The quaternary ammonium hydroxides previously mentioned are also to be regarded as salts in the context of this invention and therefore covered by this concept.

Among the ammonium salts, tetraorgano ammonium halides have been found to be particularly suitable.

Crown ethers are also suitable phase transfer catalysts for the process according to the present invention, but are less preferred. Examples of crown ethers include 1,4,7,10,13-pentaoxacyclopentadecane (15-crown-5), 1,4,7,10,13,16-hexaoxacyclooctadecane (18-crown-6), dibenzo-18-crown-6 and dicyclohexyl-18-crown-6.

In the process according to the invention, the phase transfer catalysts are used in quantities of 0.001 to 10 mole percent, preferably 0.005 to 1.0 mole percent and more preferably 0.01 to 0.2 mole percent, based on the hydroxyl groups present in the hydroxyl group-containing compounds. It is advisable to use as small a quantity of catalyst as possible in order to reduce the amount which must be removed after termination of the reaction.

The triorganochlorosilanes are used in the process according to the invention in a quantity which is at least equivalent to the hydroxyl groups which are to be silylated. It is frequently advisable to use a 5 to 300 mole percent, preferably a 20 to 100 mole percent excess of the silylating agent, based on the hydroxyl groups to be silylated.

The process according to the invention is generally carried out at a temperature of 20° to 160° C., preferably 55° to 130° C.

The reaction according to the invention is generally carried out in the absence of solvents. After the addition of the phase transfer catalysts, the compounds which are to be silylated and the triorganochlorosilane are heated to the reaction temperature, preferably the reflux temperature, and the hydrochloric acid formed is removed as a gas. Since the boiling point of the reaction mixture is not substantially higher than that of the silylating agent, if a large excess of triorganochlorosilane is used and some compounds are then not completely silylated, it is advisable in such cases to begin the reaction with only a portion of the triorganochlorosilane and then to add further triorganochlorosilane when the desired reaction temperature has been reached. In such cases, it may also be advisable to adjust the reaction temperature to the desired level by the addition of a suitable inert, high boiling solvent.

Preferred "inert organic solvents" include aliphatic, cycloaliphatic and aromatic hydrocarbons optionally substituted by halogens such as fluorine, chlorine or bromine or by nitro groups; esters; ethers; tertiary amides and sulphones; and ketones which do not enolize.

Examples of suitable solvents include isooctane, dodecane, toluene, nitrobenzene, chlorobenzene, xylene, petroleum spirits, n-butyl ethers, diphenyl ether, butyl acetate, ethyl benzoate and mixtures of such solvents.

It may be advisable in some cases to carry out the reaction according to the invention under elevated pressure since this enables higher reaction temperatures to be employed as well as enabling a larger excess of silylating agent to be used, which facilitates completion of the desired reaction.

When working up the end product, any excess of triorganosilane present may be removed by distillation. When pure starting materials are used, the pure silylated end products are obtained after removal, if necessary, of the phase transfer catalyst by filtration. Further purification may be carried out by distillation when low molecular weight starting materials have been used.

The 0-silylated hydroxyl compounds prepared according to the invention are of wide interest in organic chemistry. For example, silylation may render a product soluble in apolar solvents, thereby in many cases enabling reactions to be carried out in a homogeneous phase. Further, the volatility of organic compounds is distinctly altered by trialkyl silylation; many compounds cannot be distilled without decomposition unless silylated.

Trialkyl silyl ethers are also of interest for preparative organic chemistry. The silylated hydroxyl compounds prepared according to the invention are suitable in particular for the preparation of isocyanates containing ester groups. For this purpose, the triorganosiloxy compounds are reacted with isocyanato carboxylic acid chlorides according to the teachings of DE-OS 3 634 248; the reaction being accompanied by liberation of the silylating agent.

When tetraorgano ammonium halides are used as catalysts, which are particularly preferred, it is a great advantage that these compounds also catalyze the esterification reaction and therefore need not be removed before esterification is carried out.

Polyisocyanates which are of particular technical interest may be obtained by using the polyfunctional silylated alcohols prepared according to the invention. Such polyisocyanates are suitable as starting materials for polyurethanes, in particular for the preparation of valuable raw materials for coating compositions.

The following examples serve to illustrate the process according to the invention in more detail. All percentages given are percentages by weight unless otherwise indicated.

EXAMPLES

Example 1

1-trimethylsiloxybutane 1 mole of n-butanol and 1.5 moles of trimethylchlorosilane were heated to reflux (54°–91° C.) with the addition of 0.0005 moles of tetra-n-butyl ammonium bromide. Vigorous evolution of HCl was observed. When evolution of gas ceased, the IR spectrum did not show an OH band. When the product was worked up by distillation, pure 1-trimethylsiloxybutane was obtained as distillate.

Yield: 92%, Bp: 124°–125° C.

Example 2

2,2-dimethyl-1-trimethylsiloxypropane 1 mole of neopentyl alcohol and 1.5 moles of trimethylchlorosilane together with 0.0005 moles of tetra-n-butyl ammonium bromide were heated under reflux (54°–100° C.) until the IR spectrum did not show an OH band. The product was worked up by fractional distillation at normal pressure.

Yield: 94%, Bp: 121° C.

Example 3

Trimethylsiloxycyclohexane 1 mole of cyclohexanol, 1.5 moles of trimethylchorosilane and 0.0005 moles of tetra-n-butyl ammonium bromide were reacted at the reflux temperature (54°–97° C.) as in Example 1 and then worked up by distillation.

Yield: 95%, Bp: 56° C./15 mm.

Example 4

1,1-dimethyl-1-trimethylsiloxyethane:

1 mole of tert. butanol, 1.5 moles of trimethylchlorosilane and 0.001 moles of tetra-n-butyl ammonium bromide were reacted at the reflux temperature (54°–67° C.) as in Example 1 and then worked up by distillation.

Yield: 87%, Bp: 101°–103° C.

Example 5

1,4-bis-trimethylsiloxybutane 1 mole of butane-1,4-diol, 3 moles of trimethylchlorosilane and 0.002 moles of tetra-n-butyl ammonium bromide were reacted at the reflux temperature (54°–96° C.) as in Example 1 and then worked up by distillation.

Yield: 98%, Bp: 92°–94° C./17 mm.

Example 6

2,2-bis-trimethylsiloxymethyl-1-trimethylsiloxypropane 1 mole of trimethylol propane, 4 moles of trimethylchlorosilane and 0.003 moles of triethylbenzyl ammonium chloride were reacted at the reflux temperature (54°–104° C.) as in Example 1 and then worked up by distillation.

Yield: 96%, Bp: 124°–125° C./10 mm.

Example 7

2,2-bis-trimethylsiloxymethyl-1,3-bis-trimethylsiloxypropane 1 mole of pentaerythritol, 6 moles of trimethylchlorosilane and 0.004 moles of triethylbenzyl ammonium chloride were reacted at the reflux temperature (54°–86° C.) as in Example 1 and then worked up by distillation.

Yield: 93%, Bp: 128°–130° C./5 mm.

Example 8

1,4-bis-trimethylsiloxymethyl-cyclohexane 1 mole of cyclohexane dimethanol, 3 moles of trimethylchlorosilane and 0.002 moles of triethylbenzyl ammonium chloride were reacted at the reflux temperature (56°–100° C.) as in Example 1. When the reaction had terminated, excess silylating agent was distilled off and the precipitated catalyst was removed by filtration after cooling. The silyl ether was obtained in a quantitative yield.

Example 9

1,2,3-tris-trimethylsiloxypropane 1 mole of glycerol, 4 moles of trimethylchlorosilane and 0.003 moles of trimethylbenzyl ammonium chloride were reacted at the reflux temperature (54°–102° C.) as in Example 1. Excess silylating agent was distilled off after termination of the reaction. The catalyst was filtered off when the reaction mixture was cold.

Example 10

1,4-bis-trimethylsiloxybutane 1 mole of butane-1,4-diol, 3 moles of trimethylchlorosilane and 0.002 moles of tributyl-hexadecyl phosphonium bromide were reacted at the reflux temperature (56°–96° C.) as in Example 1. The product was worked up by fractional distillation.

Yield: 84%, Bp: 92°–94° C./17 mm.

Example 11

Preparation of a bis-trimethylsiloxy polyether 1000 g (0.5 moles) of a difunctional polyether having an OH number of 56 (prepared by the propoxylation of propylene glycol), 2 moles of trimethylchlorosilane and 0.001 moles of tetrabutyl ammonium bromide were heated under reflux (54°–96° C.) until the evolution of HCl ceased. The IR spectrum showed no OH band after completion of the reaction. Excess trimethylchlorosilane was removed from the reaction mixture by distillation under reduced pressure.

Example 12

Preparation of a bis-trimethylsiloxy polyester 850 g (0.5 moles) of a difunctional polyester having an OH number 65.9 (prepared by the condensation of adipic acid with a mixture of hexane-1,6-diol and neopentyl glycol in a molar ratio of 1.65:1) were reacted with 2 moles of trimethylchlorosilane and 0.002 moles of triethylbenzyl ammonium chloride at 54°–92° C. as in Example 11. The bis-trimethylsiloxy polyester was obtained in a quantitative yield after removal of the volatile constituents.

Example 13

Preparation of a bis-trimethylsiloxy polyester carbonate 1000 g (0.5 moles) of a difunctional polyester carbonate diol having an OH number of 56 (prepared according to DE-AS 1 770 245 by the reaction of hexane-1,6-diol with ε-caprolactone in the molar ratio of 1.1 followed by reaction of the resulting ester diol with diphenylcarbonate) were reacted with 2 moles of trimethylchlorosilane and 0.002 moles of tetra-n-butyl ammonium bromide at 54°-97° C. as described in Example 11. The silylated polyester carbonate was obtained in a quantitative yield after removal of the volatile constituents.

Example 14

Silylation of a hydroxyfunctional polyacrylate 1217 g of an 80% solution in xylene of a polyhydroxy polyacrylate having an OH number of 46 and a molecular weight ($M_w$) of 3000 (prepared by the copolymerization of 50 parts by weight of n-butyl acrylate, 34 parts by weight of 2-ethylhexyl acrylate and 10 parts by weight of hydroxyethyl acrylate in the presence of 6 parts by weight of di-t-butyl peroxide in an 80% xylene solution) were reacted as described in Example 11 with 2 moles of trimethylchlorosilane and 0.002 moles of tetra-n-butyl ammonium bromide at 60° to 91° C. After termination of the reaction, excess trimethylchlorosilane was removed from the reaction mixture by distillation.

Example 15

Silylation of castor oil 343 g of commercial castor oil having an OH number of 163 (1.0 mole of hydroxyl groups), 2 moles of trimethylchlorosilane and 0.002 moles of tetra-n-butyl ammonium bromide were heated to reflux. When the evolution of gas had ceased, the IR spectrum showed no OH band. Volatile constituents were distilled off under vacuum.

Example 16 n-butoxy-triethylsilane 0.1 moles of n-butanol, 0.15 moles of triethylchlorosilane and 0.0005 moles of triethylbenzyl ammonium chloride in 50 ml of p-xylene were heated under reflux (80°-110° C.). When the evolution of HCl had ceased, the product was worked up by fractional distillation at reduced pressure.

Yield: 68%, Bp: 70°-73° C./10 mm.

Example 17 n-butoxy-tert.-butyl-dimethylsilane 0.1 moles of n-butanol, 0.15 moles of t-butyldimethylchlorosilane and 0.0005 moles of triethylbenzyl ammonium chloride were heated under reflux (77°-106° C.) in 50 ml of p-xylene. After termination of the reaction, excess silylating agent and xylene were distilled off at reduced pressure.

Example 18

Preparation of a polyisocyanate containing ester groups according to DE-OS 3 634 248 (U.S. Ser. No. 07/105,833)

1 mole of trimethylol propane, 4 moles of trimethylchlorosilane and 0.003 moles of tetra-n-butyl ammonium bromide were heated under reflux. When the evolution of HCl had ceased, the IR spectrum showed no OH band. 3 moles of 6-isocyanatohexanoic acid chloride were rapidly added dropwise at 70° C. to the mixture which was now free from OH groups. The reaction mixture was stirred at 70° to 80° C. and excess trimethylchlorosilane as well as the trimethylchlorosilane formed in the reaction were continuously distilled from the reaction mixture. The progress of the reaction was followed using IR spectroscopy by observing the reduction in the acid chloride band. After termination of the reaction, the last residues of trimethylchlorosilane were removed by thin layer distillation and a polyisocyanate having the following properties was obtained:

viscosity: 150 mPas (22° C.)
NCO content: 21.6%.

The polyisocyanate was suitable for the preparation of low solvent 2-component polyurethane lacquers.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of an O-silylated aliphatic hydroxyl compound which comprises reacting an aliphatic hydroxyl compound with a triorganochlorosilane in the presence of a phase transfer catalyst and in the absence of a solvent, and removing the hydrogen chloride formed during the reaction from the reaction mixture in gaseous form.

2. The process of claim 1 wherein said phase transfer catalyst comprises a member selected from the group consisting of quaternary organic ammonium salts, quaternary organic phosphonium salts and crown ethers.

3. The process of claim 1 wherein said phase transfer comprises a member corresponding to the formula:

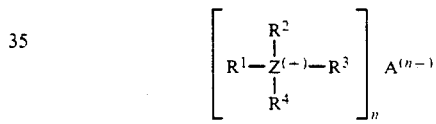

wherein
Z represents nitrogen or phosphorus,
$R^1$, $R^2$, $R^3$ and $R^4$ may be identical or different and represent aliphatic, cycloaliphatic, aromatic or araliphatic hydrocarbon groups, provided that the sum of the carbon atoms in these groups is 8 to 28,
n represents 1 or 2 and
A represents an n-valent anion of an acid or a hydroxide anion.

4. The process of claim 3 wherein
Z represents nitrogen,
$R^1$, $R^2$, $R^3$ and $R^4$ may be the same or different and represent aliphatic hydrocarbon groups having 1 to 18 carbon atoms, phenyl groups or benzyl groups, provided that the sum of the carbon atoms in these groups is 8 to 24 and at least three of the groups are aliphatic hydrocarbon groups,
n represents 1 and
A represents a bromide, chloride or iodide ion.

5. The process of claim 1 wherein said triorganochlorosilane comprises a member corresponding to the formula

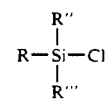

wherein

R', R" and R'" may be the same or different and represent alkyl groups having 1 to 4 carbon atoms.

6. The process of claim 4 wherein said triorganochlorosilane comprises a member corresponding to the formula

wherein

R', R" and R'" may be the same or different and represent alkyl groups having 1 to 4 carbon atoms.

7. The process of claim 1 wherein said triorganochlorosilane comprises trimethylchlorosilane.

8. The process of claim 4 wherein said triorganochlorosilane comprises trimethylchlorosilane.

9. The process of claim 1 wherein said aliphatic hydroxyl compound comprises at least one monohydric to octahydric alcohol having a molecular weight of 32 to 342.

10. The process of claim 4 wherein said aliphatic hydroxyl compound comprises a hydroxyl group-containing polyaddition, polycondensation or polymerization product having molecular weights greater than 342.

11. A process for the preparation of a compound containing at least one isocyanate group and at least one ester group which comprises preparing an O-silylated hydroxyl compound in accordance with the process of claim 1 and reacting said O-silylated hydroxyl compound with an isocyanatocarboxylic acid chloride to form said compound containing at least one isocyanate group and at least one ester group.

* * * * *